(12) United States Patent
Jones et al.

(10) Patent No.: US 6,888,127 B2
(45) Date of Patent: May 3, 2005

(54) METHOD AND APPARATUS FOR PERFORMING RAPID ISOTOPIC ANALYSIS VIA LASER SPECTROSCOPY

(75) Inventors: Christopher Jones, Houston, TX (US); Zvi Sofer, Houston, TX (US); Richard J. Drozd, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 34 days.

(21) Appl. No.: 10/083,282

(22) Filed: Feb. 26, 2002

(65) Prior Publication Data

US 2003/0160164 A1 Aug. 28, 2003

(51) Int. Cl.[7] ............................................. G01N 21/35
(52) U.S. Cl. .............................. 250/269.1; 250/339.13
(58) Field of Search ....................... 250/269.1, 339.13, 250/345, 346, 350, 351

(56) References Cited

U.S. PATENT DOCUMENTS

| | | | |
|---|---|---|---|
| 4,492,862 A | | 1/1985 | Grynberg et al. |
| 4,517,461 A | | 5/1985 | Crandall |
| 4,922,747 A | * | 5/1990 | Wall .......................... 73/61.41 |
| 4,951,287 A | | 8/1990 | Wyeth et al. .................. 372/32 |
| 4,990,780 A | | 2/1991 | Lee et al. .................... 250/343 |
| 5,317,156 A | | 5/1994 | Cooper et al. ............... 250/345 |
| 5,445,964 A | * | 8/1995 | Lee et al. ...................... 436/60 |
| 5,543,621 A | * | 8/1996 | Sauke et al. ........... 250/339.03 |
| 5,640,014 A | | 6/1997 | Sauke et al. ........... 250/339.03 |
| 5,747,809 A | * | 5/1998 | Eckstrom .................... 250/345 |
| 5,841,533 A | | 11/1998 | Atkinson .................... 356/326 |
| 5,864,398 A | | 1/1999 | Murnick ..................... 365/311 |
| 5,929,112 A | | 7/1999 | Higashi .................. 250/339.13 |
| 5,957,858 A | | 9/1999 | Micheels et al. ........... 600/529 |
| 6,202,470 B1 | | 3/2001 | Chou |
| 6,483,589 B1 | | 11/2002 | Suzuki |
| 2001/0025927 A1 | | 10/2001 | Ankerhold |

FOREIGN PATENT DOCUMENTS

| | | | | |
|---|---|---|---|---|
| DE | 19962589 | 7/2001 | .......... | G01N/37/00 |
| EP | 0 426 232 A2 | 4/1991 | | |
| EP | 1111369 | 6/2001 | | |
| EP | 1111370 | 6/2001 | | |
| JP | 4364442 | 12/1992 | | |
| JP | 5340872 | 12/1993 | | |
| JP | 6018411 | 1/1994 | | |
| JP | 11094737 | 4/1999 | | |
| JP | 9297061 | 7/1999 | | |

OTHER PUBLICATIONS

Uehara et al., *Isotope Analysis of Environmental Substances by a New Laser–Spectroscopic Method Utilizing Different Pathlengths*, Sensors and Actuators B 74 (2001) pp. 173–178.

Becker et al., *Stable Isotope Analysis Using Tunable Diode Laser Spectroscopy*, Applied Optics, Apr. 20, 1992, vol. 31, No. 12, pp. 1921–1927.

European Search Report for European Application No. EP 03 25 5126, dated Jun. 4, 2003 (3 p.).

* cited by examiner

*Primary Examiner*—Constantine Hannaher
*Assistant Examiner*—Otilia Gabor
(74) *Attorney, Agent, or Firm*—Conley Rose, P.C.

(57) ABSTRACT

Method and apparatus for providing real-time data indicative of the isotopic composition of formation fluids during drilling. The method includes the steps of: (a) providing a reference fluid having a known isotopic composition in a reference cell; (b) capturing a sample of formation; (c) providing at least one laser beam; (e) passing a beam through the reference fluid, measuring the reference-measurement beam before and after it passes through the reference fluid; (f) and passing a beam through the sample, measuring the beam before and after it passes through the sample, and calculating a first isotope concentration from those measurements. The measurements can provide information relating to the carbon isotopic composition of individual compounds in hydrocarbon gas mixtures, with the individual compounds including methane, ethane, propane, iso- or normal butane, or iso- or normal pentane.

22 Claims, 1 Drawing Sheet

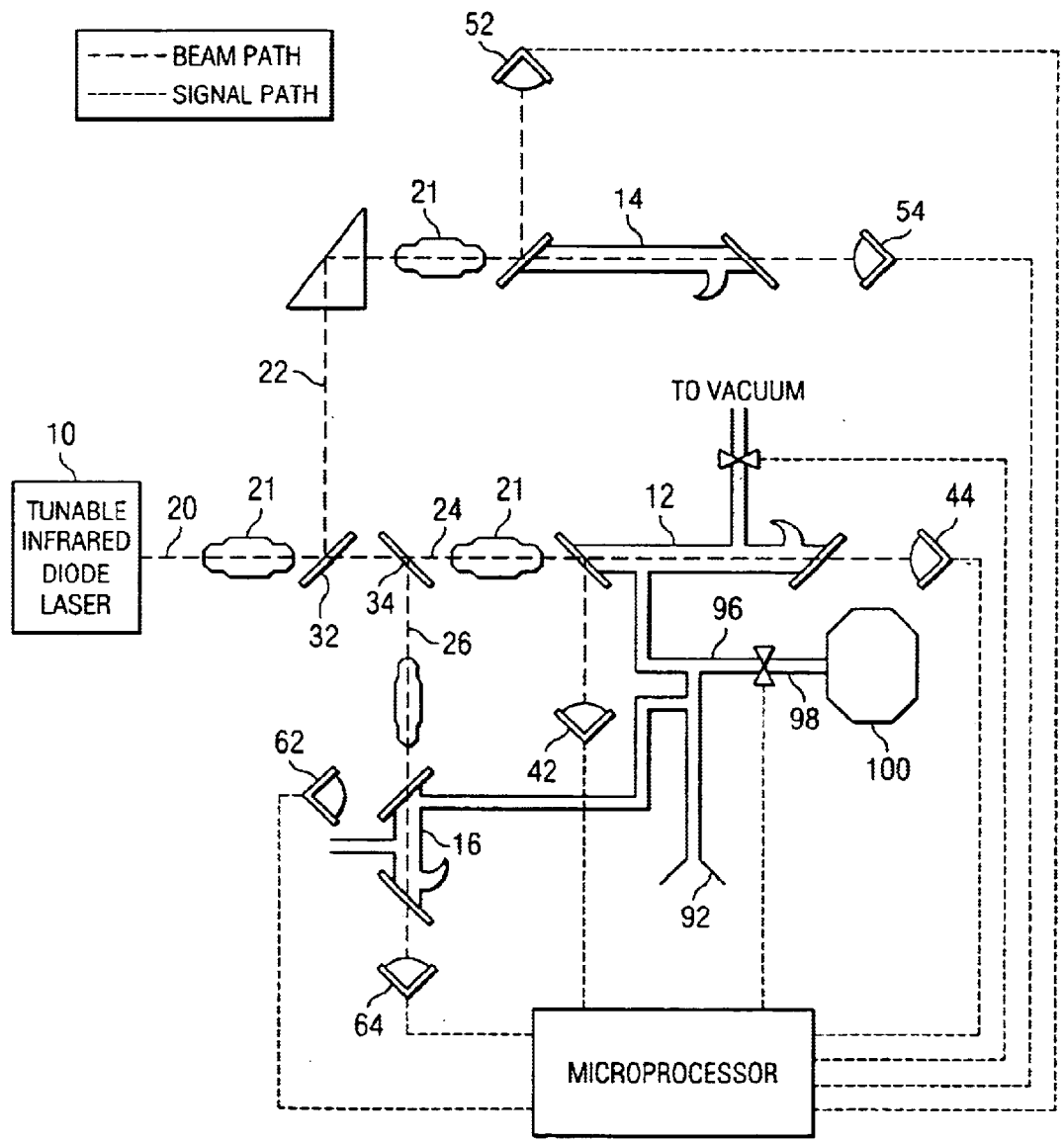

METHOD AND APPARATUS FOR PERFORMING RAPID ISOTOPIC ANALYSIS VIA LASER SPECTROSCOPY

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD OF THE INVENTION

The present invention relates generally to the use of lasers to perform rapid isotopic analysis so as to gain information about the composition of a substance or mixture. More particularly, the present invention relates to a novel method and apparatus that can be used to quickly and easily determine the relative amounts of two or more isotopes in a mixture comprising unknown amounts of each isotope. Still more particularly, the present patent application describes a new process and a new instrument for analyzing the carbon and hydrogen isotopic composition of individual compounds in hydrocarbon gas mixtures, including but not limited to: methane, ethane, propane, iso- and normal butane, and iso- and normal pentane.

BACKGROUND OF THE INVENTION

Both academic and industrial research institutes have extensively studied stable isotopic compositions of various elements in petroleum. The commonly studied elements include carbon, hydrogen, sulfur, nitrogen and oxygen. Isotopic compositions of individual components of natural gases, whole crude oils, crude oil fractions and solids have been determined. The most commonly studied element is carbon ($^{13}C/^{12}C$), distantly followed by hydrogen (D/H).

Mass Spectrometry

Various techniques for quantitatively or qualitatively determining isotopic composition are known. For example, certain types of isotope ratio determinations are commonly done on mass spectrometers that have been specifically designed for that purpose. Such instruments can determine the isotopic ratios of a limited number of gases: $H_2$, $N_2$, $CO_2$ (for $^{13}C/^{12}C$ and $^{18}O/^{16}O$ ratios), $SO_2$ and $SF_6$. Therefore, when it is desired to determine the isotopic ratios of organic and inorganic compounds containing these elements, the compounds must be first quantitatively converted to the appropriate gas. Determination of $HD/H_2$ and $^{13}C/^{12}C$ ratios in organic compounds requires the combustion of the sample (usually in the presence of hot CuO) to $CO_2$ and water, cryogenic separation of the water from the $CO_2$ and conversion of the water over hot metal shavings (U, Zn, Cr or Mn). In some cases, organic hydrogen is directly converted to elemental hydrogen by pyrolysis over hot metal shavings (Cr or Mn). The resulting gases then can be analyzed on the mass spectrometer. These steps typically require very labor intensive preparation procedures and the use of costly mass spectrometers specifically designed for isotope ratio determinations.

Specifically, for natural hydrocarbon gases, the gas mixture must first be separated into its individual compounds. This is typically accomplished by means of a gas chromatograph (GC) using helium as a carrier gas. The separated gases flow into a hot tube furnace (900° C.) packed with copper oxide, where the individual gases are quantitatively converted to $CO_2$ and water. Once the separated compounds have emerged at the end of tube furnace, there are two methods to determine the isotopic composition of the individual compounds.

In the first, older method, the $CO_2$ and water from the individual compounds are diverted into individual detachable cold traps, where they are frozen. Once all the components have been collected, the cold traps are transferred to a purification line, where the helium is pumped out and the $CO_2$ is cryogenically separated from the water. The pure $CO_2$ is then cryogenically trapped in a "transfer tube" and transferred to the mass spectrometer (MS) where the $^{13}CO_2/^{12}CO_2$ ratio is determined. The water is transferred into a reduction tube, where it is quantitatively converted to hydrogen gas, which is then analyzed by the mass spectrometer for $H_D/H_2$ ratios. The whole process is labor intensive and only a few of the steps have been automated. The mass spectrometer is normally "tuned" to analyze $CO_2$ samples. When enough water samples have been collected, it is "tuned" for $H_D/H_2$ analysis. Switching between $CO_2$ and hydrogen tuning involves at least half a day of down time.

In the second method (called GCIRMS—GC Isotope Ratio Mass Spectrometry) the system is adapted to analyze either $CO_2$ or hydrogen. For $CO_2$, at the end of the tube furnace the helium/$CO_2$/$H_2O$ mixture is passed through a water trap then, the helium/$CO_2$ mixture is directly injected into the mass spectrometer where the $^{13}CO_2/^{12}CO_2$ ratio is determined. This method requires significantly smaller samples, however the duration of the $^{13}CO_2/^{12}CO_2$ ratio determination is much shorter (the width of the GC peak) resulting in less accurate ratios. The duration of the complete analysis (methane to pentane) is determined by length of time required to elute all the components through the GC. In order to determine the $HD/H_2$ ratio, the water trap is removed and the copper oxide tube furnace is replaced by a pyrolysis tub furnace where the gases are converted to elemental carbon and hydrogen gas. The hydrogen gas is then analyzed with the appropriate tuning of the MS in a similar fashion to $CO_2$.

The hydrogen isotope analysis is a relatively new technique and is not commonly used. All mass spectrometers have a relatively narrow dynamic range, which is often smaller than the range of concentrations that occurs in natural gas mixtures. Therefore, in order to determine all components using a GCIRMS instrument, it is often necessary to inject the same sample several times, varying the sample size with every injection to fit the concentration of each components into the dynamic range of the MS.

In addition, mass spectrometers and the associated preparation lines are costly, heavy and bulky. They include many glass and quartz parts and require continues supply of high purity helium and liquid nitrogen. Therefore, they cannot readily be "ruggedized" for on site field operations. Also, because of the length of time required for complete compound analyses, they cannot provide real time data, often needed in field operations.

Gas Chromatography

Gas chromatographs that detect the presence of hydrocarbon gases encountered during drilling have been deployed on drilling rigs for many years. However, these instruments are slow and often inaccurate and therefore do not permit instantaneous collection information regarding the hydrocarbon composition of the gases. No instrument that can be deployed to a drilling rig site for the purpose of rapid carbon and hydrogen isotope analyses is available on the market to date, let alone isotopic composition.

Isotopic Analysis Using Molecular Vibrations

Isotopic ratio measurements via quantum vibrational transitions have existed for many years. The two main measurement methods are based on emission spectra and absorption spectra. Initially, quantitative determination of isotopic ratios via the emission spectra of molecular transitions was inaccurate and not useful. At the same time, the absorption spectra lacked the resolution needed to characterize overlapping but isotopically different molecular transitions. This was mainly due to lack of power at monochromatic wavelengths. With the advent of lasers in the late 1960's, this limiting factor was eliminated, and high-resolution characterization of polyatomic species with isotopic substitution was possible. It was not until the completion of laser absorption studies in controlled laboratory settings that quantitative emission studies became useful. The primary focus of isotopic laser studies on short chain hydrocarbons, specifically methane, was characterization of spectroscopic properties for astronomical purposes. It was through these studies that the carbon isotopic composition of methane in extraterrestrial planetary atmospheres was first determined via emissions detected during near passes of artificial satellites in the late 1970's.

Laser isotopic studies of carbon in methane and other short chain hydrocarbons continued for academic purposes until the late 1980's. In the 1990's, little scientific work was done in the field of carbon isotopic measurements in hydrocarbon gases. Since the 1990's, the academic focus has shifted to laser isotopic studies of inorganic polyatomic molecules. To date, however, the only commercialized applications of $^{13}C/^{12}C$ measurements have been in medical research (measuring exhaled carbon dioxide), and in geological research for determining inorganic characterization of water and carbon in sandstone/mudstones, pyrite, sphalerite, galena and calcite. In the analysis of exhaled $CO_2$, light emitted by a $CO_2$ laser is used to measure isotope ratios. It should be noted that, to date, the determination of $^{13}C$ for geological purposes has been applied only to carbonate rocks. Inorganically bound isotopes of sulfur, oxygen, and hydrogen have also been studied with lasers for geological and environmental purposes.

Analysis in Laser-Based Systems for Pollution Purposes

Determination of absolute concentration of trace levels (low ppb range) of atmospheric gasses using laser technology has been the focus of current academic and commercial research. Gasses currently studied are $H_2O$, $CO_2$, CO, NO, $NO_2$, $N_2O$, $SO_2$, $CH_4$, $C_2H_2$, HF, HCL, HBr, HI, HCN, $H_2S$, $O_3$, $NH_3$, $H_2CO$, $PH_2$, $O_2$, OCS, $C_2H_6$, $C_3H_8$, $C_4H_{10}$, although gasses above $C_2$ have only been studied in laboratory settings. Of the hydrocarbon gases, only $CH_4$ has been studied isotopically, and purely for academic purposes. Most research has been conducted for environmental ends, but detection of these molecules for monitoring leaks from industrial processes has also been of interest and commercial laser spectrometers for these purposes have been developed.

On-Site Field Analyses

Wells are often drilled for the purpose of extracting hydrocarbons from formations deep in the earth. In many cases, there is a variety of strata between the surface and the target formation. Some of these may contain hydrocarbons, of which it may be desirable to determine the isotopic composition. In addition, it is often desirable to determine the isotopic composition of the hydrocarbons in the target formation itself. Furthermore, it is often desirable to analyze isotopic composition during production, as well as during drilling and post-production. The downhole environment is very harsh, with high temperatures and pressures, and often corrosive liquids or gasses. The ruggedness of the downhole and well-site environments, their remoteness, and space constraints make it difficult to devise instruments that are capable of making direct analyses on the formation fluids.

Historically, the stability of the laser spectrometer has limited the usefulness of isotopic measurements via laser spectroscopy. New laser systems are available with very high repetition rates and better stability. Despite the existence of the foregoing technologies, a need still exists for very accurate real time hydrocarbon analysis in the context of drilling. It would also be desirable to provide a system for measuring the structural position of the isotopically substituted element.

SUMMARY OF THE INVENTION

The method and apparatus of the present invention can be used advantageously for a multitude of purposes, including but not limited to: analyzing formation fluids in the context of petroleum drilling operations, analyzing hydrocarbon streams in petroleum refining and other operations, and making accurate and precise measurements of various biomaterials in the contexts of medical diagnosis and treatment.

The present invention comprises method and apparatus for determining the amount of a carbon isotope in a fluid. A preferred embodiment of the apparatus includes a laser source emitting a laser beam, a beam splitter receiving the laser beam and emitting first and second beams, a volume of the fluid, through which the first beam passes, a downstream optical detector positioned to detect the first beam after it passes through the first volume, a reference cell containing a known concentration of the isotope, through which the second beam passes and a second downstream optical detector positioned to detect the second beam after it passes through the reference cell. The first optical detector emits a first downstream signal corresponding to the strength of the first beam after it passes through the first volume and the second optical detector emits a second downstream signal corresponding to the strength of the second beam after it passes through the reference cell. The tool further includes a microprocessor that receives the first and second downstream signals and calculates therefrom the a parameter indicative of the presence of the isotope in the fluid.

In particular preferred embodiments, the first fluid volume is contained in a cell, or in a conduit in which the fluid may be flowing or static. The tool can be configured so that the sample cell and the reference cell are at substantially the same temperature, the sample volume and the reference cell can be located in a wellbore when said first and second beams pass through them, respectively, or the sample volume and the reference cell can be outside of a wellbore when the measurement beams pass through them. In further embodiments, the microprocessor calculates a concentration of the isotope in the fluid relative to the concentration of the isotope in the reference cell or calculates a quantitative concentration of the isotope in the fluid. In still further embodiments of the tool, the laser source is a tunable laser source. The present device can be used to measure the presence of a carbon isotope when the carbon isotope is part of a hydrocarbon.

In still further embodiments, the present apparatus includes a first upstream detector that detects the first beam before it passes through the sample volume and emits a corresponding first upstream signal; and a second upstream detector that detects the second beam before it passes through the reference cell and emits a corresponding second upstream signal.

In still further embodiments, the microprocessor receives the upstream signals and uses them in calculating said parameter indicative of the presence of the isotope in the fluid. In some embodiments, the downstream signals are indicative of the transmittance of said first and second measurement beams through said sample and reference cells, respectively.

In other embodiments, the present invention comprises a method for providing real-time data indicative of the isotopic composition of a hydrocarbon fluid, and includes the steps of (a) providing a reference fluid having a known isotopic composition in a reference cell, (b) defining a sample of the hydrocarbon fluid, (c) providing a laser beam, (d) splitting the beam to form a reference-measurement beam and a sample-measurement beam, (e) passing the reference-measurement beam through the reference fluid, measuring said reference-measurement beam after it passes through said reference fluid, (f) passing the sample-measurement beam through the sample, measuring the sample-measurement beam after it passes through the sample; and (g) calculating a parameter indicative of the presence of the isotope in the fluid using measurements made in steps (e) and (f).

In particularly preferred embodiments of the method, step (b) comprises placing the sample of the hydrocarbon fluid in a cell or a conduit. The fluid in the conduit can be either flowing or static during measurement. The microprocessor in step (g) can calculate a concentration of the isotope in the fluid relative to the concentration of the isotope in the reference cell or a quantitative concentration of the isotope in the fluid. The measurements can be used to provide information relating to the carbon isotopic composition of individual compounds in a hydrocarbon gas mixture, and particular can be used to obtain information about the presence of methane, ethane, propane, iso- and normal butane, and iso- and normal pentane.

In still further embodiment, the present method can be carried out where steps (e) and (f) are carried out at substantially the same temperature, or are carried out in a wellbore, or the sample can be obtained from a wellbore but steps (e) and (f) can be carried out outside of the wellbore.

BRIEF DESCRIPTION OF THE DRAWINGS

For a more detailed understanding of the preferred embodiments, reference will be made to the accompanying FIGURE, which is a schematic diagram of an apparatus constructed in accordance with the present invention.

DETAILED DESCRIPTION OF THE INVENTION

Advances in laser spectroscopy have included the advent of the mid- and far-infrared tunable diode laser, which was developed for and has been used primarily by the telecommunications industry since the early 1990's. Because these wavelengths overlap the absorption region of many molecular vibrational modes of the carbon-hydrogen bond in hydrocarbons, they can be utilized to detect such molecules.

Other advances include the modification of these lasers for ultra-short pulses approaching single wavefronts (femptosecond pulses). Rapid firing capabilities have been developed for diode lasers currently allow generation of up to many thousands of stable shots per second over long periods of time. New electronic schemes for internal and external power stabilization of lasers have also been developed. It is the combination of these advancements that now allow rapid high resolution analysis of steady state fluid systems.

According to the present invention, laser spectroscopy is facilitated by new detectors and power stabilization techniques to monitor isotopically the molecular components of a fluid system by monitoring the ro-vibrational transitions of the species of interest in real time. The present invention has particular utility for the petroleum industry, as it provides a means to monitor the carbon and hydrogen isotopic composition with accuracy that is as good as or better than the current industry standard. In addition to real time in situ determinations, the present laser technology has the capability to make measurements as to the structural position of the isotopically substituted element.

According to a preferred embodiment, signal stabilization for the precise quantification of a sample is accomplished by splitting the direct output of one laser beam into multiple beams of known intensity. As discussed in detail below, one beam passes through the sample cell to a first detector while another passes directly onto an identical second detector and or through a reference cell and then onto an identical third detector. The observed difference in the detected beam intensities can be translated into either absolute or relative concentrations of molecular species and or into absolute or relative concentrations of isotopic species.

Ro-vibrational profiles are dependent on spectral constants of molecular states. One physical property on which these constants depend is the mass of the molecule. Thus, one observes a different wavelength of absorption for isotopically differing species of identical elemental and structural composition. One also observes differing absorption characteristics for isotopically different species.

The system of the present invention determines isotopic compositions of individual hydrocarbons in a fluid based on the different optical properties of individual hydrocarbons with and without heavy atom ($^{13}$C and D) substitution on the molecule. The present instrument and process completely eliminate any need for manual sample preparation. Measurements can be made directly on the gas of interest without the need to quantitatively convert it first to $CO_2$ and/or $H_2$ and without the need remove other hydrocarbon and non-hydrocarbon gases from the mixture. In a preferred embodiment, the present instrument and process allow the simultaneous determination of $^{13}C/^{12}C$ and or D/H ratios of all relevant hydrocarbon components in the gas mixture. In some cases, information as to the position of the isotope-substituted element in molecules larger than $C_2$, which is lost upon combustion, may be obtained using this technology.

By using a reference cell, the present invention is able to quantify the absolute concentration of both isotopic species individually or to determine their relative concentrations more accurately. This is accomplished by monitoring a distinct ro-vibrational absorption line (and not necessarily of the same quantum transition) from each chemically identical but different isotopic species. According to Beer's law, the ratio of absorbed intensities for each line is proportional to the ratio of concentrations of the species and a multiplication constant relating the different absorption characteristics of the two quantum transitions. Using a reference cell with a gas of known isotopic composition eliminates the need to know the Beer's law absorption constant, since that constant will be identical for any transition monitored in the sample as well as the reference. The reference cell also allows a more accurate determination of isotopic enrichment or depletion relative to the reference gas because the absolute isotopic ratio of the reference gas need not be known. For determinations that are more accurate, the entire rotational profile of a vibrational transition or multiple ro-vibrational transitions may be monitored.

Referring now to the FIGURE, a preferred embodiment of the present system includes an optical measurement system 10 and a sample-processing system 11. Optical measurement system 10 preferably includes a tunable laser source 10, a reference cell 12, a sample cell 14, and a pre-dilution cell 16. Reference cell 12 includes a pair of optical detectors 42, 44 positioned at its inlet and outlet, respectively. Similarly, sample cell 14 includes optical detectors 52, 54 and pre-dilution cell 16 includes optical detectors 62, 64. Optical detectors 42, 44, 52, 54, 62, 64 preferably include a beam splitter where necessary and a sensor for measuring the amount of incident light, such as are well known in the art. The sample cell 12 may either be a static or steady state system. In some instances sample cell 12 may actually be inserted into the laser cavity, or be omitted altogether.

It will be understood that, while the gas-containing volume through which the laser beam(s) are passed are referred to herein generally as "cells," they do not need to comprise an enclosed or finite volume. For example, the light used to measure the presence of an isotope can be passed through a conduite or line in which the material to be measured flows continuously. Similarly, a measuring beam can be passed through a sample volume that is not contained in a finite volume, such as when the measuring beam is passed through a gas-containing space and used to assess the gas in the space.

For each cell or other volume of interest, the amount of light absorbed by the material therein can be determined by comparing the measurements made by inlet and outlet detectors at that cell. In an alternative embodiment (not shown), the inlet and outlet beams for each cell can all be directed to and measured by a single optical measuring device. The advent of femtosecond lasers and detectors makes it possible to use path length and signal arrival time to differentiate between separate signals received at a single measuring device.

Still referring to the FIGURE, sample-processing system 11 preferably includes a sample inlet 92, a pre-dilution line 94, a sample line 96, a dilution line 98 and a diluent source 100. Inlet 92 receives the fluid that is to be analyzed by the present apparatus. Pre-dilution line 94 provides fluid communication between inlet 92 and pre-dilution cell 16. Sample line 96 provides fluid communication between inlet 92 and sample cell 14. Dilution line 98 provides fluid communication between dilution source 100 and sample line 96. Sample-processing system 11 also preferably includes vacuum lines 97, 99 for emptying pre-dilution cell 16 and sample cell 14, respectively.

Flow through the apparatus is preferably but not necessarily continuous. It is may also be further preferred to provide one or more optics boxes 21 in the path of one or more beams. The optics boxes can, as is known in the art, be used to telescope the beam, expanding (or decreasing) its diameter and correspondingly decreasing (or increasing) its intensity.

In operation, a fluid sample enters inlet 92 and a portion of it is diverted into pre-dilution cell 16. Optical measurements of the fluid are made using detectors 62, 64 and information about the undiluted sample is transmitted to a microprocessor (not shown). The microprocessor in turn determines whether and to what degree the fluid needs to be diluted. Because increased pressure causes a broadening of the transition profile for a given measured compound, it may be necessary or preferred to dilute the sample so as to decrease the partial pressure of the compound being measured and thereby increase the resolution of the resulting measurements, particularly if the line broadening is such that it is not possible to distinguish the peaks of the compounds in question without enhancing resolution.

If it is desirable to dilute the sample, the microprocessor causes diluent source 100 to release a predetermined amount of diluent at a predetermined rate into sample line 96. Nitrogen ($N_2$) is by far the most preferred diluent, with alternative diluents including but not limited to: argon, boron, or other noble gases. The diluent and the sample mix in sample line 96 and the diluted sample flows into sample cell 14. Because the objective is to lower the partial pressure of one or more components of the sample, an alternative to dilution is to expand the gas in the sample, thereby lowering its total pressure and thus, correspondingly, the partial pressure of all of its components.

Laser source 10 preferably emits a light beam 20 having a short duration, preferably from about 2 to about 10 nanoseconds (nsec). A series of beam splitters 32, 34 splits beam 20 into three beams 22, 24, 26, and directs the three beams 22, 24, 26 into reference cell 12, sample cell 14, and pre-dilution cell 16, respectively. As used herein beam splitters 32, 34 can use any device capable of splitting the beams, including multiplexing. It is not necessary that the beam used to measure the predilution sample come from the beam used to measure the sample and reference. Some of the light entering each cell is absorbed by the material therein. The amounts of light that are absorbed in the reference and sample cells are determined and the amounts are compared. The ratio of the absorption amounts in the reference and sample cells can be easily and directly correlated with the isotopic composition of the reference and sample fluids.

In another embodiment, the beam is not split. Instead, a single beam, or a portion thereof, is passed through both the reference cell and the sample cell. Alternatively, the fluid volumes can be positioned such that each fluid volume receives a distinct or separate portion of the beam, without the beam being split. Regardless of whether the beam is split, and regardless of which cell the beam passes through first, the effect of each cell on the light passing through that cell is measured and quantified and the resulting data are used in the manner described above to generate information about the presence of the isotope in the sample cell.

The present device is preferably a small instrument, preferably occupying less than about 25 cubic feet, that is sufficiently rugged to be used both in the field and in laboratory systems, where it can replace traditional natural gas isotope analytical setups. An important application for the present invention is its deployment on drilling rigs exploring for oil and gas, where it eliminates the to need collect samples and ship them to the lab for analyses. Nonetheless, the present device can be used advantageously in many other applications, including but not limited to: environmental monitoring, pipeline/shipping management, spill identification and "fingerprinting." The use of lasers and the elimination of costly, complicated and bulky preparation systems reduces the analysis time from hours to seconds. This in turn allows virtually instantaneous information and can thus improve the efficacy of various drilling decisions. In environmental applications, where sampling density and sample size are problems, the present device provides the ability to easily collect large data sets that can be used to distinguish naturally occurring natural gases from man-made contamination and pinpoint contamination sources.

The instrument preferably has a very wide dynamic range of detection to allow the analyses of extremely diluted hydrocarbon gases without the need to concentrate the gases of interest. Another advantage of the present system is that, because it includes a dilution system, it can analyze a greater range of concentrations, since it can use a very dilute reference volume and dilute a wide range of sampled fluids down to that concentration level.

The present invention uses a combination of sensitive detectors and detection schemes, precise electronic gating systems, computing technology and algorithms to provide rapid isotopic analysis via laser spectroscopy of any simple molecule and of short chain hydrocarbons in particular. Detector systems that use algorithms to self-correct are commercially available and are preferred for use in the present system. Other new technologies enhance the practicality of the present system. For examples, narrow time gates, more stable lasers, more stable time gating equipment, and more powerful microprocessors make it possible to use smaller sample and to analyze the sample more quickly and effectively than was heretofore possible.

Two primary laser techniques can be used for the isotopic ratio analysis and absolute quantification of simple molecules. One detects Laser Induced Florescence (LIF) and the other detects changes in laser beam intensity (absorption). Although LIF is more sensitive, it is harder to use as a quantitative technique because multiple molecular quantum states must be simultaneously assessed with a high degree of resolution. In addition, technical factors make use of a reference cell difficult. Therefore the present system is described in reference to an absorption system.

The laser(s) used in the present invention may be either continuous wave or pulsed. Semiconducting diode lasers are most common for industrial purposes and therefore readily commercially available, however gas lasers, excimer lasers, and dye lasers have also been employed. Lasers are chosen based on characteristics of power, polarization, coherency, bandwidth, stability, Q-switch repetition rate, wavelength regime and maintenance. Semiconducting diode lasers are preferred because they tend to be mostly maintenance free. They have large power capabilities, narrow bandwidths and are very stable, making them most attractive to industry. For the present device, a laser with a high repetition rate (around 10 KHz), with a 3% shot to shot stabilization or less, and is tunable over the absorption band of hydrocarbons fundamental vibrational modes is most desired. Multiple lasers may be employed if a combination of lasers cover the entire wavelength regions of interest. Because tunable infrared diode lasers meet the general criteria they are the focus of this design, however the design is applicable to any laser present or future that meets these criteria.

For gas detection, a single rotational line of a vibrational transition (ro-vibrational) is chosen for monitoring. The wavelength of the laser is set to the energy of that transition. The amount of light absorbed by a species at a specific wavelength is proportional to the concentration of that species, the distance that the radiation travels through the absorption medium, and an absorption constant (Beer's Law). This relationship holds true for a species with well-resolved spectral lines, no nonlinear interference, and laser intensities below the optical saturation level for systems without broadening effects. As the species absorbs radiation, its concentration can be calculated from the amount of radiation transmitted, the distance the radiation traversed the medium, and the absorption constant of that specific transition at a given wavelength. Much effort is spent designing laser spectrometers systems for which Beer's law or a variation thereof is valid.

Temperature and pressure are the conditions that most affect the application of Beer's law for the quantification of concentration via EM radiation absorption. Beer's law measures the concentration difference of species between two particular quantum states. It is assumed that the concentration difference between two quantum states is proportional to the concentration of the species as a whole. Populations of vibrational and rotational states (those states which are primarily measured by the absorption of infrared radiation) vary with temperature. Therefore in the direct application of Beer's law through external calibration either the full set of spectroscopic constants for the quantum states of interest must be predetermined, an empirical correction curve for correction with temperature must be derived, or the calibration must be carried out at the same temperature as the sample. The latter approach is used in the present invention. Temperature also has higher order effects which may be ignored for normal operating conditions. One higher order effect is the Doppler width of a transition. The Doppler width increases with temperature. It is preferred to have the sample at the natural Doppler limit, so as to avoid making the measurements unnecessarily complex. Therefore, to avoid errors due to a changing Doppler width, it is desirable to hold the sample's temperature as constant as possible.

Pressure has the major effect of broadening a transition profile. For this reason, determination of concentration via Beer's law requires either the full set of spectroscopic constants to be determined, an empirical correction curve to be derived, or isobaric conditions between the sample and calibration set. Again, the latter is most often employed. Higher order pressure effects may often be ignored under normal operation. With the assumption that the vibrational state population does not vary to a significant state with temperature, one may monitor the entire ro-vibrational profile of calibration sets and samples without the need of temperature or pressure correction. This process however, is much too time-consuming to be practical in a real-time scenario.

The present invention eliminates the need for complete spectral monitoring or correction by splitting the direct output of the laser and directing one of the resulting beams into an added reference cell. Under these conditions, the only requirement is that the reference cell be at the same temperature and total pressure as that of the sample. The underlying assumption is that the ratio of the absorption of the sample to the reference species at a monochromatic wavelength is proportional to that of the concentrations of the sample to the reference. This follows from Beer's law. Although this is similar to a one point external calibration, a simultaneous measurement offers several advantages. One advantage is that quantification errors due to minute variations of the laser wavelength are negated, as Beer's absorption coefficient varies identically for a simultaneous measurement of sample and reference. In order to make absolute concentration determination it is necessary to know the distance that the light travels through the sample and the reference cells and the absorption constant. In practice, though, the two constants are usually combined and determined experimentally, with known standards substituted into the positions of the sample and reference cell. Once normalized with one or more standards, the device is ready to make absolute or relative concentration determinations.

In an alternative, less preferred, embodiment, the present invention can be practiced in the absence of a reference cell. In this embodiment, an external calibration curve is determined with respect to concentration, temperature, and pressure. Some nonlinear temperature effects could be alternatively be dismissed by monitoring the entire ro-vibrational transition as stated above.

The spectral properties of a particular transition change with pressure. Specifically, the wavelength of the transition varies with pressure, as does the bandwidth of the transition. Again, the bandwidth can be accounted for by monitoring the entire spectral profile of the ro-vibrational transition although this is too time-consuming to be practical for this application.

There is a more practical assumption one can make about pressure effects, which greatly simplifies the device's design. This refers to the Doppler line width limit. This is the temperature dependent limit for which line width of a quantum transition due to pressure broadening is a minimum. Broadening of line profiles is caused by molecular and atomic collisions of species with each other. Therefore, a reduction in the number of collisions reduces the line width. The collisions actually perturb and relax the quantum state for which species exists. Therefore not all quantum states have the same Doppler limit, or are effected by collisions in the same way, even within the same species. The limit of decreased line with at a given temperature is the Doppler limit.

Not all species collide in the same way or are as effective at broadening the line profile as other species. In general however, when one lowers absolute pressure of the system, fewer collisions take place and therefore the line profile of the species narrows. Likewise, if the pressure of a species that is less likely to broaden is increased relative to the pressure of those species that are more likely to broaden while the total pressure remains constant then the line profile will also become narrower. This last technique is called buffering, and in the case of the a compressible fluid the species that are used to decrease the line profile while keeping the total pressure constant are often referred to as the buffer gas. Some buffer gasses have the capacity to lower a line width to the Doppler limit at ambient pressure. Sometimes a combination of buffering and reduced pressure is most efficient. There is some evidence, at least for methane, that nitrogen could be an effective buffer gas and allow an ambient pressure determination of methane gas. The same information is not known for the other gasses of interest. In every case, a reduced total pressure would narrow the line profile for an analytical determination of that gas.

It is the design of the pre-dilution step in the preferred embodiment to either introduce a buffer gas or reduce the total pressure of the system, for the purpose of decreasing the line width of the transitions of interest below that of the Doppler line with. This is necessary for two reasons. First, line broadening is a nonlinear effect which can affect the application of Beer's law. It is experimentally easiest to ensure that the system is below the Doppler limit, as opposed to employing pressure correction factors or ensuring that the partial pressure, which is unknown, is identical to that of the reference. Second, lines due to molecular transitions of bonds between normal elements and isotopic elements will be shifted relative to molecular transitions of bonds between normal elements and normal elements for chemically identical species. However, the shift will be very small compared to the normal range of pressure broadened line widths. Therefore, if the line profile for the transition of interest is too wide, it will overlap with the isotopically shifted line, breaking the requirement for Beer's law that the transitions be spectrally well resolved. Since line shifting is a smaller effect, it usually can be ignored.

While the present disclosure addresses the analysis of short chain hydrocarbons, the present technique can be applied to hydrocarbons larger than $C_4$ and to other molecules. However, with increasing hydrocarbon size, the natural line width reaches a size that will overlap with the isotopically shifted transition. Also the vibrational structure of the spectra become increasingly complex and convoluted. Therefore, for species of increasing molecular size, well resolved isotopically shifted molecular lines will be harder to find. Without experimentation, it is difficult to determine the practicable limit of hydrocarbon size for this technique. It is possible that additional research will allow this instrument to determine the isotopic ratio of hydrocarbons above $C_5$ while preserving the information relating to the substituted carbon. This information has never been collected before and the application of this new type of data may be very valuable to the petroleum industry. Such a device though would most certainly have to include variations designed to force less volatile hydrocarbons into the gas phase, such as increased temperature at the sampling chamber and greatly reduced pressure.

Hence, potential applications for the present system include but are not limited to: drilling rigs where natural gases are encountered while drilling, environmental testing, such as swamp gases, detection of leakage from gas transmission lines, and other instances where it is desirable to obtain near-instantaneous information about the isotopic composition of a fluid. In addition, the ability to identify the position of the isotope-substituted element in $C_{3+}$ molecules may open new avenues of research as to the origin, thermal maturity and mixing of natural gases in the subsurface.

What is claimed is:

1. A tool for determining the amount of a carbon isotope in a fluid, comprising:

a laser source emitting at least one laser beam;

a first volume of the fluid positioned so that at least a first portion of a laser beam passes through the fluid;

a first downstream optical detector positioned to detect said first beam portion after said first beam portion passes through said first volume, said first optical detector emitting a first downstream signal corresponding to the strength of said first beam portion after passing through the first volume;

a reference cell containing a concentration of the isotope and positioned so that at least a second portion of a laser beam passes through said concentration;

a second downstream optical detector positioned to detect said second beam portion after said second beam portion passes through said reference cell, said second optical detector emitting a second downstream signal corresponding to the strength of said second beam portion after passing through said reference cell;

a pre-dilution cell containing a portion of the fluid positioned so that at least a third portion of a laser beam passes through the portion of the fluid;

a third downstream optical detector positioned to detect said third beam portion after said third beam portion passes through said pre-dilution cell, said third downstream optical detector emitting a third downstream signal corresponding to the strength of said third beam portion after passing through the pre-dilution cell; and a microprocessor receiving said first, second, and third downstream signals and calculating from the first and second downstream signals a parameter indicative of the presence of the isotope in the fluid, and wherein the microprocessor determines from the third downstream signal whether and to what degree to dilute the fluid with a diluent.

2. The tool according to claim 1, wherein said first and second beam portions comprise a single beam.

3. The tool according to claim 1 wherein said first and second beam portions comprise separate beams.

4. The tool according to claim 1 wherein said first fluid volume is contained in a cell.

5. The tool according to claim 1 wherein said first fluid volume is contained in a conduit.

6. The tool according to claim 1 wherein said microprocessor calculates a concentration of the isotope in the fluid relative to the concentration of the isotope in the reference cell.

7. The tool according to claim 1 wherein said microprocessor calculates a quantitative concentration of the isotope in the fluid.

8. The tool according to claim 1 wherein the reference cell contains an unknown concentration of the isotope.

9. The tool according to claim 1, wherein the reference cell contains a known concentration of the isotope.

10. The tool according to claim 1, further including a first upstream detector detecting said first beam portion before said first beam portion passes through said first volume and emitting a corresponding first upstream signal; a second upstream optical detector detecting said second beam portion before said second beam portion passes through said reference cell and emitting a corresponding second upstream signal; and a third upstream optical detector detecting said third beam portion before said third beam portion passes through the pre-dilution cell and emitting a corresponding third upstream signal.

11. The tool according to claim 1 wherein said microprocessor receives said first, second, and third upstream signals and uses said first and second upstream signals in calculating said parameter indicative of the presence of the isotope in the fluid, and wherein said microprocessor uses said third upstream signal in determining whether and to what degree to dilute the fluid with the diluent.

12. The tool according to claim 1 wherein the diluent comprises nitrogen.

13. The tool according to claim 1, wherein the diluent comprises at least one of nitrogen and at least one noble gas.

14. A tool for determining the amount of a carbon isotope in a fluid, comprising:

a laser source emitting at least one laser beam;

a first volume of the fluid positioned so that at least a first portion of a laser beam passes through the fluid;

a first upstream optical detector positioned to detect said first beam portion before said first beam portion passes through said first volume, said first optical detector emitting a first upstream signal corresponding to the strength of said first beam portion before passing through the first volume;

a first downstream optical detector positioned to detect said first beam portion after said first beam portion passes through said first volume, said first optical detector emitting a first downstream signal corresponding to the strength of said first beam portion after passing through the first volume;

a reference cell containing a concentration of the isotope and positioned so that at least a second portion of a laser beam passes through said concentration;

a second upstream optical detector positioned to detect said second beam portion before said second beam portion passes through said reference cell, said second optical detector emitting a second upstream signal corresponding to the strength of said second beam portion before passing through the reference cell;

a second downstream optical detector positioned to detect said second beam portion after said second beam portion passes through said reference cell, said second optical detector emitting a second downstream signal corresponding to the strength of said second beam portion after passing through said reference cell; and a microprocessor receiving said first and second upstream and downstream signals and calculating therefrom a parameter indicative of the presence of the isotope in the fluid.

15. The tool according to claim 14 wherein said first and second beam portions comprise a single beam.

16. The tool according to claim 14 wherein said first and second beam portions comprise separate beams.

17. The tool according to claim 14 wherein said first fluid volume is contained in a cell.

18. The tool according to claim 14 wherein said first fluid volume is contained in a conduit.

19. The tool according to claim 14 wherein said microprocessor calculates a concentration of the isotope in the fluid relative to the concentration of the isotope in the reference cell.

20. The tool according to claim 14 wherein said microprocessor calculates a quantitative concentration of the isotope in the fluid.

21. The tool according to claim 14 wherein the reference cell contains an unknown concentration of the isotope.

22. The tool according to claim 14, wherein the reference cell contains a known concentration of the isotope.

* * * * *